United States Patent [19]

Bolesky

[11] Patent Number: 4,955,910
[45] Date of Patent: Sep. 11, 1990

[54] FIXATION SYSTEM FOR AN ELONGATED PROSTHESIS

[75] Inventor: Richard C. Bolesky, Warsaw, Ind.

[73] Assignee: Boehringer Mannheim Corporation, Indianapolis, Ind.

[21] Appl. No.: 380,998

[22] Filed: Jul. 17, 1989

[51] Int. Cl.$^5$ .............................................. A61F 2/08
[52] U.S. Cl. ........................................ 623/13; 623/11
[58] Field of Search ............................... 623/13, 11, 16

[56] References Cited

U.S. PATENT DOCUMENTS

| | | |
|---|---|---|
| 3,953,896 | 4/1976 | Treace . |
| 4,187,558 | 2/1980 | Dahlen et al. . |
| 4,246,660 | 1/1981 | Wevers ................................. 623/13 |
| 4,301,551 | 11/1981 | Dore et al. . |
| 4,708,132 | 11/1987 | Silverstrini . |
| 4,712,542 | 12/1987 | Daniel et al. ......................... 623/13 |
| 4,744,793 | 4/1988 | Parr et al. . |
| 4,755,183 | 7/1988 | Kenna . |
| 4,772,286 | 9/1988 | Goble et al. . |
| 4,776,851 | 10/1988 | Bruchman et al. ................... 623/13 |
| 4,828,562 | 5/1989 | Kenna .................................... 623/13 |
| 4,870,957 | 10/1989 | Goble et al. ........................... 623/13 |

FOREIGN PATENT DOCUMENTS 2614123  10/1977  Austria ................................... 623/13

Primary Examiner—Randall L. Green
Assistant Examiner—David H. Willse
Attorney, Agent, or Firm—Perman & Green

[57] ABSTRACT

A fixation system is disclosed for an elongated prosthesis such as a prosthetic ligament. Opposed ends of the ligament are attached to spaced apart bones such that the connections are external of the bones so as to permit a maximum of relative movement between the ligament and the bones while assuring requisite strength in tension. The design enables pretensioning of the ligament, guards against abrasion of the ligament by reason of moving contact with the bones, and is adjustable to accommodate a variety of required sizes.

14 Claims, 2 Drawing Sheets

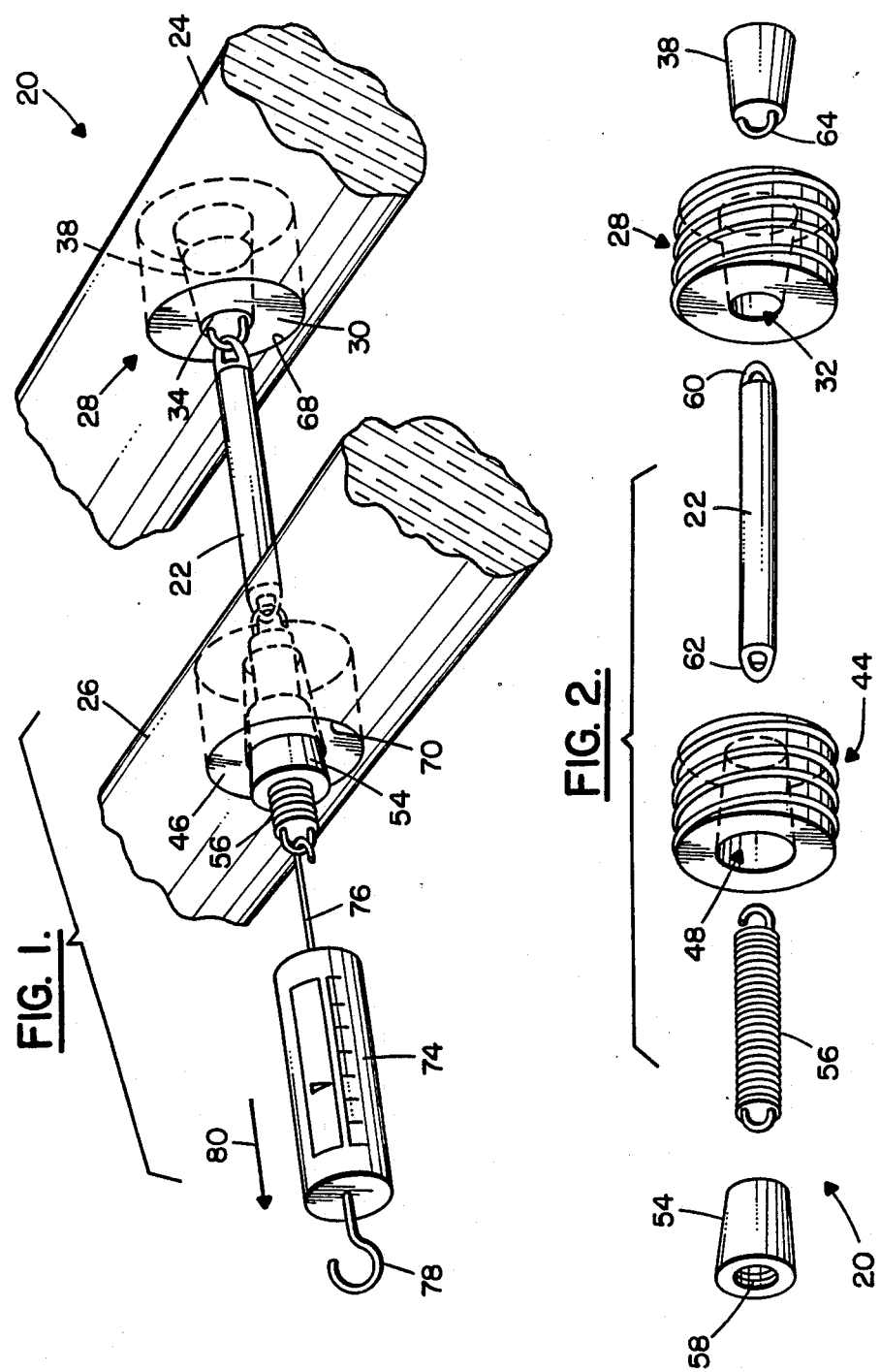

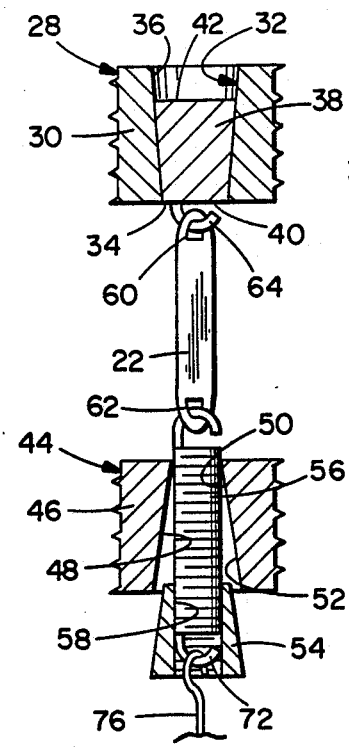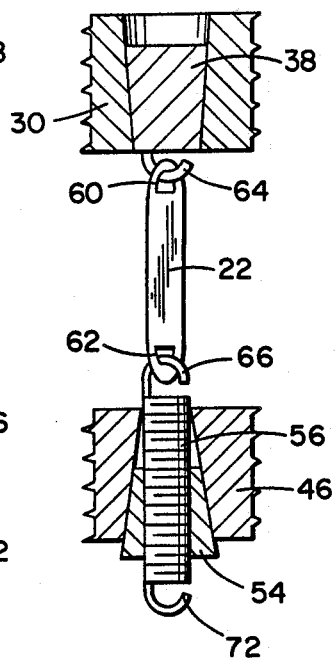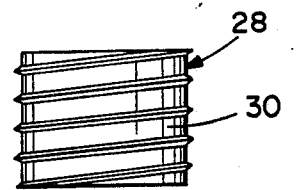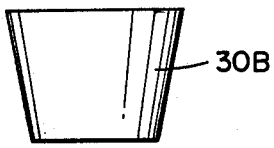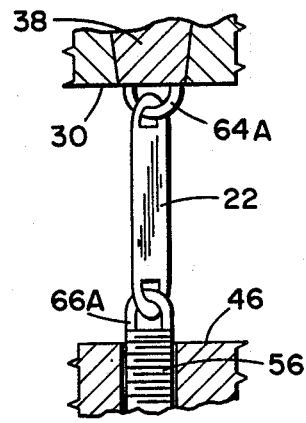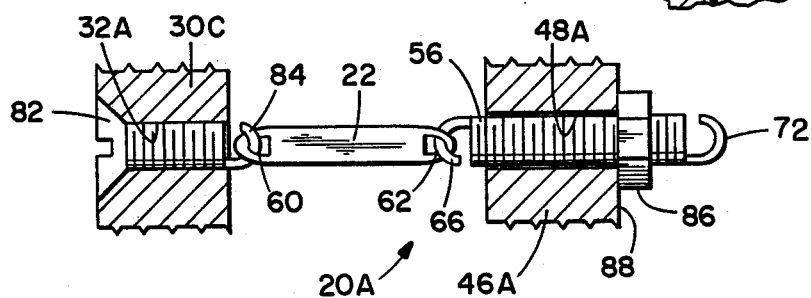

FIXATION SYSTEM FOR AN ELONGATED PROSTHESIS

BACKGROUND OF THE INVENTION

1. Field of the Invention

The present invention relates generally to prosthetic devices and, more particularly, to a fixation system for an elongated prosthesis which approximates the characteristics of the natural ligament or tendon being replaced.

Ligaments are strong, flexible fibrous cords or bands that fasten bones together Tendons are similar cords or bands that attach muscles to bones or other structures. The concept of the invention is the same whether it be in the context of a ligament or of a tendon. Therefore any reference in the text to a ligament may generally be taken to mean a tendon, and vice versa, unless the usage clearly indicates otherwise.

2. Description of the Prior Art

Since skeletal ligaments flexibly stabilize joints, they must withstand considerable amounts of force. Frequently, the skeletal ligaments are subjected to enough force to be torn or otherwise damaged, thereby resulting in instability of the joint. This results in pain and possible damage to other tissues. Although some torn ligaments can be repaired by simply sewing the torn ends together, such repair is not always possible in cases of severe damage or disease. Further, surgical repair is not always predictable and requires a healing period of minimal stress before the ligament can again be functionally useful.

The above circumstances have led to the development of a variety of artificial ligaments. A wide variety of elongated prostheses have been proposed for the repair or replacement of diseased or damaged ligaments and tendons. Examples of such prostheses, including devices to secure their ends, can be seen in any of the patents to Treace, U.S. Pat. No. 3,953,896, to Dahlen et al, U.S. Pat. No. 4,187,558, to Dore et al, U.S. Pat. No. 4,301,551, to Silvestrini, U.S. Pat. No. 4,708,132, to Parr et al, U.S. Pat. No. 4,744,793, to Kenna, U.S. Pat. No. 4,755,183, and to Goble et al, U.S. Pat. No. 4,772,286.

Although prosthetic ligaments have a variety of outward appearances, they commonly consist of a flexible longitudinal material having two end portions. The end portions are used to firmly attach the ligament to two adjoining bones such as, for example, the lower femur and the upper tibia. In use, the flexible central portion of the prosthetic ligament is subjected to repeated flexing, stress, and, in some cases, abrasion against bone edges. This can result in deterioration and possible rupture of the prosthesis.

One of the significant problems associated with the design of an artificial ligament or tendon prosthesis is the proper design of the means for fixation of the prosthesis to the patient's bone structure, typically with the prosthesis in a state of pretension. Such a fixation device should be securely held to the bone and should be capable of firmly gripping a portion of the prosthesis without damaging it. In particular, it is important that the prosthesis and fixation device not interact in use in such a way as to significantly detract from the inherent fatigue resistance of the active prosthesis structure itself. This may occur, for example, by excessive abrasive wear between the prosthesis and the fixation device.

SUMMARY OF THE INVENTION

It is therefore an object of the present invention to provide a system for the fixation of a pretensioned ligament or tendon prosthesis to spaced apart bones of a patient, in particular, a prosthesis which is simple in construction and easy to use, is securely held to the patient's bones with the prosthesis in a pretensioned state, and which is capable of securely gripping the prosthesis without damaging it, which would significantly detract from the fatigue resistance of the prosthesis or otherwise adversely affect the performance of the prosthesis in vivo.

These and other objects of the invention are achieved with a novel fixation system according to which opposed ends of the ligament are attached to spaced apart bones such that the connections are external of the bones This construction serves to permit a maximum of relative movement between the ligament and the bones while assuring requisite strength in tension. The design enables pretensioning of the ligament, guards against abrasion of the ligament by reason of moving contact with the bones, and is adjustable to accommodate a variety of required sizes The design further controls tension of the ligament within the joint rather than between external bone surfaces.

In a preferred embodiment, the invention utilizes a pair of retention members which may be attached to the opposed bones between which the ligament is to extend. Each retention member may be threadedly engaged with the bone or cemented in a suitable manner to the bone. In one embodiment, a first retention member is fixed to a first bone and, is formed with a tapered bore which can receive a similarly shaped attachment member. The attachment member has an integral loop at its end facing the second bone. In a similar manner, the second retention member is suitably fixed to the second bone and also formed with a tapered bore adapted to slidably receive an externally threaded anchor member which, similar to the attachment member, has a loop member at its end facing the first bone. The prosthetic ligament includes integral loop members at its opposite ends which are encircled with the loop members at the ends of the first attachment member and the anchor member. A second attachment member is threadedly received on the anchor member. As it is turned, it advances into engagement with the tapered bore of the second retention member until a predetermined magnitude of tension in the prosthetic ligament is achieved.

A number of other embodiments are disclosed but all achieve the desired objectives mentioned above.

The invention, in all of its embodiments, is of a simplified construction which utilizes known materials and can be readily implanted.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and, together with the description, serve to explain the principles of the invention in general terms. Like numerals refer to like parts throughout the disclosure.

BRIEF DESCRIPTION OF THE DRAWINGS

FIG. 1 is a detail perspective view of a prosthetic ligament assembly embodying the invention;

FIG. 2 is an exploded perspective view illustrating components of the prosthetic ligament assembly depicted in FIG. 1;

FIGS. 3 and 3A are diagrammatic cross sectional views of the prosthetic ligament assembly of the invention illustrating successive steps in the attachment procedure;

FIGS. 4A, 4B, and 4C are detail side elevational views depicting various embodiments of one component of the invention;

FIGS. 5A, 5B, and 5C are cross section views depicting another component of the invention;

FIG. 6 is a cross sectional diagrammatic view of a preferred construction of the prosthetic ligament assembly of the invention; and FIG. 7 is a detail cross sectional view illustrating another embodiment of the assembly illustrated in FIGS. 3A and 6.

DETAILED DESCRIPTION OF THE PREFERRED EMBODIMENTS

Turn now to the drawings and, initially, to FIGS. 1 and 2 which illustrate a fixation system 20, generally embodying the invention, for an elongated prosthesis 22. The prosthesis 22 is in the form of a ligament extending between a pair of spaced apart bones, 24 and 26, respectively. A first retention mechanism 28 is fixed to the bone 24 and includes a grommet 30. As seen especially well in FIGS. 3 and 4A, the grommet 30 may be cylindrical and externally threaded thereby enabling its entry into the bone 24 either from the side facing the prosthesis 22 or from the opposite side, as appropriate.

The grommet 30 may take other forms, however. For example, as seen in FIG. 4B, a grommet 30A may be tapered and threaded. In still another embodiment, as illustrated in FIG. 4C, a grommet 30B may be frusto-conical in shape, intended for cemented fixation into an appropriately prepared cavity within the bone. In its tapered configuration, the grommet 30B may also be porous coated to encourage bone ingrowth. Of course, in the instance of either grommet 30A or grommet 30B, the smaller diameter end is positioned to face the prosthesis 22.

Returning especially to FIG. 3, the grommet 30 is formed with a through bore 32 which extends between a minor opening 34 of reduced cross sectional area facing toward the bone 26 and a major opening 36 facing away from the bone 26. The bore 32 defines a seating surface for a similarly tapered attachment member 38 also extending between a minor end 40 of reduced cross sectional area and a major end 42 of enlarged cross sectional area. Of course, it will be appreciated that, in all instances the major and 42 is greater in magnitude than the minor opening 34 in the grommet 30.

In a somewhat similar fashion, a retention mechanism 44 is fixed to the second bone 26. As with the retention mechanism 28, the retention mechanism 44 includes a grommet 46 which may alternatively be of any of the constructions illustrated with respect to grommet 30 in FIGS. 4A, 4B, and 4C. That is, it may similarly be cylindrical and threaded, or tapered and threaded, or tapered without threads. Furthermore, as with the grommet 30, the grommet 46 also has a through bore 48 extending between a minor opening 50 of reduced cross sectional area facing toward the bone 24 and a major or opening 52 of increased cross sectional area facing away from the bone 24. Also, as in the instance of the grommet 30, bore 48 defines a frusto-conical seating surface for a similarly shaped attachment member 54.

An elongated cylindrical externally threaded anchor member 56 is seen in FIG. 3 to extend through the bore 48. The tapered attachment member 54 has a longitudinally extending threaded bore 58 for threaded engagement with the anchor member 56.

The prosthesis 22 may be composed of any suitable material, for example, fiber, metal, polymer, or any combination thereof. Furthermore, the prosthesis 22 may be formed with any cross section appropriate for its particular use and location in the body. Typical cross sections are illustrated in FIGS. 5A, 5B, and 5C. The opposite ends of the prosthesis 22 include integral loop members 60 and 62 for attachment, respectively, to the attachment member 38 and anchor member 56. To this end, the attachment member 38 includes an integral loop member 64 generally facing the bone 26 for linked reception with loop member 60 on the prosthesis 22. In like manner, the anchor member 56 includes an integral loop member 66 generally facing the bone 24. The loop member 66 is positioned for linked reception with the loop member 62 on the prosthesis 22.

Although the loop members 64 and 66 are generally illustrated as being open to enable attachment of the prosthesis to the attachment member 38 and to the anchor member 66, they may be subsequently deformed to prevent subsequent disengagement of the prosthesis. That is, on a one time basis, the free end of the loop member 64 would be forced into engagement with the minor end 40. In a similar manner, the free end of the loop member 66 would be forced into engagement with its associated end of the anchor member 56.

A preferred construction is illustrated in FIG. 6 in which loop members 64A, 66A are formed so as to be completely closed and unitary with its respective member 38, 56. In this instance, the prosthesis 22 would be suitably molded or otherwise fashioned into linked engagement with the members 38, 56.

In the course of the surgical procedure for implanting the fixation system 20, again viewing FIG. 1, a pair of opposed bores 68, 70 are formed, respectively, in the bones 24, 26. In the event the system has the FIG. 6 construction, the anchor member 56 is threaded through the bore 32 followed by the prosthesis 22 and the attachment member 38 which advances into seating engagement with the bore 32. The anchor member 56 continues to proceed through the bore 48 of the grommet 46, drawing with it the prosthesis 22. The attachment member 54 is then threadedly engaged with the anchor member 56 and advanced until an integral loop member 72 on an end of the anchor member 56 opposite the loop member 56 becomes exposed.

At this point, a suitable extensiometer 74 is engaged with the loop member 72 by means of a hook 76 (FIGS. 1 and 3). Using a handle 78 at a distant end of the extensiometer 74, the surgeon draws the extensiometer in the direction of an arrow 80 thereby applying tension to the prosthesis 22. When a predetermined magnitude of tension has been applied to the prosthesis 22 which is generally in keeping with normal body conditions, the attachment member 54 is threadedly advanced until it becomes firmly seated on the bore 48. Thereupon, the extensiometer 74 can be released from the loop member 72 and the prosthesis 22 will continue to exhibit the tension originally imparted to it by means of the extensiometer.

Although the bores 32 and 48 in the grommets 30 and 46, respectively, have been described as being frusto-conical in shape, other configurations are possible FIG. 7 is illustrative of a modified system 20A according to which a grommet 30C is provided with a tapped bore 32A for threadedly receiving a screw 82 having a loop member 84 for linked engagement with the loop member 60 of the prosthesis 22. An anchor member 56, unchanged from the previous embodiment, extends through a cylindrical modified bore 48A. However, in this instance, in place of the tapered attachment member 54, a nut 86 is threadedly received on the anchor member 56 and engages an aft surface 88 of the grommet 46A. In this construction, the screw 82 serve to rigidly fix the loop member 84 to the grommet 30C and, in turn, to the bone 24 while the nut 86 serves to apply and maintain the tension desired in the prosthesis 22.

While preferred embodiments of the invention have been disclosed in detail, it should be understood by those skilled in the art that various other modifications may be made to the illustrated embodiments without departing from the scope of the invention as described in the specification and defined in the appended claims.

I claim:

1. A prosthetic ligament assembly for connecting first and second spaced apart bones comprising:
   first retention means fixed to the first bone having a first bore therethrough extending between a minor opening of reduced cross sectional area facing toward the second bone and a major opening of increased cross sectional area facing away from the second bone, the bore defining a first seating surface therein;
   said first retention means including a first attachment member having a minor end of reduced cross sectional area and a major end of increased cross sectional area shaped similarly to said first seating surface for mating engagement therewith, said major end of said first attachment member being greater in magnitude than the minor opening in said first retention means;
   second retention means fixed to the second bone having a second bore therethrough extending between a minor opening of reduced cross sectional area facing toward the first bone and a major opening of increased cross sectional area facing away from the first bone, the second bore defining a frusto-conical second seating surface;
   an elongated prosthetic ligament extending between first and second ends and being attached at said first end to said first attachment member; and
   said second retention means including adjustable mounting means for selectively attaching said second end of said prosthetic ligament to said second retention means to achieve a predetermined tension therein.

2. A prosthetic ligament assembly as set forth in claim 1
   wherein said adjustable mounting means includes:
   an elongated cylindrical externally threaded anchor member attached at one end to said second end of said prosthetic ligament and extending through the second bore in said second retention means; and
   a second attachment member frusto-conical shaped similarly to the bore in said second retention means and having a threaded bore extending therethrough for threaded engagement with said anchor member;
   enabling said second frusto-conical attachment member to be screwed into mating engagement with said second seating surface until the predetermined magnitude of tension in said prosthetic ligament is achieved.

3. A prosthetic ligament assembly as set forth in claim 1
   wherein said first seating surface is a frusto-conical surface; and
   wherein said first attachment member is frusto-conical shaped.

4. A prosthetic ligament assembly as set forth in claim 1
   wherein said first retention means is generally cylindrical, being externally threaded for fixation to the first bone and having a longitudinal axis, the first bore being aligned with said longitudinal axis; and
   wherein said second retention means is generally cylindrical, being externally threaded for fixation to the second bone and having a longitudinal axis, the second bore being aligned with said longitudinal axis.

5. A prosthetic ligament assembly as set forth in claim 2
   wherein said first and second ends of said prosthetic ligament include loop members integral therewith;
   wherein said anchor member includes a loop member at said one end linked with said loop member at said second end of said prosthetic ligament; and
   wherein said first attachment member includes a loop member at said minor end linked with said loop member at said first end of said prosthetic ligament.

6. A prosthetic ligament assembly as set forth in claim 2 including:
   first coupling means external of the first bone for connecting said first attachment member to said prosthetic ligament to resist tensile loading therebetween while otherwise permitting relative movement between said first attachment member and said prosthetic ligament; and
   second coupling means external of the second bone for connecting said anchor member to said prosthetic ligament to resist tensile loading therebetween while otherwise permitting relative movement between said anchor member and said prosthetic ligament.

7. A prosthetic ligament assembly as set forth in claim 6
   wherein said first coupling means includes a first pair of mutually linked loop members integral, respectively, with said first attachment member and with said prosthetic ligament; and
   wherein said second coupling means includes a second pair of mutually linked loop members integral, respectively, with said anchor member and with said prosthetic ligament.

8. A prosthetic ligament assembly for connecting first and second spaced apart bones comprising:
   an elongated prosthetic ligament extending between first and second ends;
   first retention means fixed to the first bone having a first bore extending therethrough between a minor opening of reduced cross sectional area facing toward the second bone and a major opening of increased cross sectional area facing away from the second bone, the bore defining a first seating surface therein, said first retention means including a first attachment member having a minor end of reduced cross sectional area and a major end of increased cross sectional area shaped similarly to said first seating surface for mating engagement therewith, said major end of said first attachment member being greater in magnitude than the minor opening in said first retention means;

second retention means fixed to the second bone having a second bore extending therethrough between a minor opening of reduced cross sectional area facing toward the first bone and a major opening of increased cross sectional area facing away from the first bone, the second bore defining a frusto-conical second seating surface therein, said second retention means including adjustable mounting means for selectively attaching said second end of said prosthetic ligament to said second retention means to achieve a predetermined tension therein;

first coupling means external of the first bone for connecting said first end of said prosthetic ligament to said first retention means to resist tensile loading therebetween while otherwise permitting relative movement therebetween; and second coupling means external of the second bone for connecting said second end of said prosthetic ligament to said second retention means to resist tensile loading therebetween while otherwise permitting relative movement therebetween.

9. A prosthetic ligament assembly as set forth in claim 8 wherein said adjustable mounting means includes:

an elongated cylindrical externally threaded anchor member attached at one end to said second end of said prosthetic ligament and extending through the second bore in said second retention means; and a second attachment member frusto-conical shaped similarly to the bore in said second retention means and having a threaded bore extending therethrough for threaded engagement with said anchor member; enabling said second frusto-conical attachment member to be screwed into mating engagement with said second seating surface until the predetermined magnitude of tension in said prosthetic ligament is achieved.

10. A prosthetic ligament assembly as set forth in claim 8 wherein said first seating surface is a frusto-conical surface; and wherein said first attachment member is frusto-conical shaped.

11. A prosthetic ligament assembly as set forth in claim 8 wherein said first retention means is generally cylindrical, being externally threaded for fixation to the first bone and having a longitudinal axis, the first bore being aligned with said longitudinal axis; and wherein said second retention means is generally cylindrical, being externally threaded for fixation to the second bone and having a longitudinal axis, the second bore being aligned with said longitudinal axis.

12. A prosthetic ligament assembly as set forth in claim 9 wherein each of said first and second ends of said prosthetic ligament includes a loop integral therewith;

wherein said anchor member includes a loop member at said one end linked with said loop member at said second end of said prosthetic ligament; and wherein said first attachment member includes a loop member at said minor end linked with said loop member at said first end of said prosthetic ligament.

13. A prosthetic ligament assembly as set forth in claim 8 wherein said first coupling means includes a first pair of mutually linked loop members integral, respectively, with said first attachment member and with said prosthetic ligament; and wherein said second coupling means includes a second pair of mutually linked loop members integral, respectively, with said anchor member and with said prosthetic ligament.

14. A prosthetic ligament assembly for connecting first and second spaced apart bones comprising:

an elongated prosthetic ligament extending between first and second ends;

first retention means having a threaded bore therethrough fixed to the first bone and including a first attachment member threadedly engaged with the threaded bore, said first attachment member including an integral loop member generally facing the second bone; and second retention means having a smooth bore therethrough fixed to the second bone and including an externally threaded second attachment member slidably received in the smooth bore, said second attachment member including an integral loop member generally facing the first bone and a nut fastener threadedly engaged with said second attachment member;

said prosthetic ligament including integral loop members at said first and second ends, respectively, mutually linking said loop members on said first and second attachment members enabling said nut fastener to be screwed into mating engagement with said second retention means until a predetermined magnitude of tension in said prosthetic ligament is achieved.

* * * * *